United States Patent [19]
Giaever et al.

[11] Patent Number: 5,187,096
[45] Date of Patent: Feb. 16, 1993

[54] CELL SUBSTRATE ELECTRICAL IMPEDANCE SENSOR WITH MULTIPLE ELECTRODE ARRAY

[75] Inventors: Ivar Giaever, Schenectady; Charles R. Keese, Schoharie, both of N.Y.

[73] Assignee: Rensselaer Polytechnic Institute, Troy, N.Y.

[21] Appl. No.: 742,439

[22] Filed: Aug. 8, 1991

[51] Int. Cl.$^5$ .................. G01N 27/02; C12M 1/34; C12M 1/20
[52] U.S. Cl. ............................ 435/291; 435/301; 435/33; 435/40; 324/692; 324/439; 204/403
[58] Field of Search ............... 435/291, 300, 32, 33, 435/34, 40, 301; 204/403; 324/439, 446, 692

[56] References Cited

U.S. PATENT DOCUMENTS

| | | | |
|---|---|---|---|
| 3,743,581 | 7/1973 | Cady et al. | 435/33 |
| 3,890,201 | 6/1975 | Cady | 435/291 |
| 4,072,578 | 2/1978 | Cady et al. | 435/33 |
| 4,156,180 | 5/1979 | Annen et al. | 435/291 |
| 4,160,205 | 7/1979 | Hobbs et al. | 435/291 |
| 4,200,493 | 4/1980 | Wilikins et al. | 435/291 |
| 4,264,728 | 4/1981 | Wilkins | 435/34 |
| 4,335,206 | 6/1982 | Wilkins et al. | 435/291 |
| 4,920,047 | 4/1990 | Giaever et al. | 435/4 |

OTHER PUBLICATIONS

Proc. Natl. Acad. Sci. USA, vol. 81, pp. 3761-3764, Jun. 1984.
IEEE Tran. on Bio med. Eng., vol. BME-33 No. 2 Feb. 1986.
Physican D 38 (1989) 128-133.
J. Imm. Methods, 127 (1990) 71-77.

*Primary Examiner*—Robert J. Warden
*Assistant Examiner*—T. A. Trembley
*Attorney, Agent, or Firm*—Notaro & Michalos

[57] ABSTRACT

An apparatus and method for monitoring cell-substrate impedance comprises upper and lower substrates each containing strips of metal foil which cross to form well areas. Holes in the upper substrate expose an insulation layer between the upper and lower substrates. Smaller holes in the insulation layer expose the conductive material of the lower substrate. Cylindrical well walls are positioned around each of the holes in the upper substrate and define a cell medium containing well which is exposed to an annular area of conductive foil on the upper substrate, and a small area of conducive foil on the lower substrate. The areas of foil form large and small electrodes which are positioned in an array of wells which can be used to monitor the impedance of various cell cultures under various conditions. A switching device applies currents to the well electrodes and a monitoring device measures the impedance between the electrodes in each well. In this way, cell spreading and motility can be measured.

12 Claims, 5 Drawing Sheets

CELL SUBSTRATE ELECTRICAL IMPEDANCE SENSOR WITH MULTIPLE ELECTRODE ARRAY

FIELD AND BACKGROUND OF THE INVENTION

The present invention relates to a device for monitoring the activities of living cells in tissue culture using electronic means.

Some aspects of electrical monitoring of cells in culture have been disclosed by the present inventors in the scientific literature. Many of the capabilities and potential applications of this technique in medicine and biotechnology, have not been disclosed however. The inventors' earlier work which has ultimately led to the present invention is disclosed in *Proc. Natl. Acad. Sci. USA*, Vol. 81, pp. 3761-3764, June 1984; *IEEE TRANSACTIONS OF BIOMEDICAL ENGINEERING*, Vol. BME-33 No. 2, February 1986; *Physica* D38 (1989) 128-133; and *Journal of Immunological Methods*, 127 (1990) pp. 71-77.

These articles do not disclose multiple electrode arrays that conform to more conventional tissue culture practice. Such electrode arrays would allow one to easily make measurements of several individual tissue cultures. Such multiple measurements would find use in many areas including in vitro toxicology, drug discovery, and drug efficacy measurements. These publications also do not disclose the use of a range of applied AC frequencies to obtain information regarding the spaces between the cell and substratum and the permeability of confluent cell layers.

Currently, electrical devices are known for measuring some activities of cells in culture. The best known of these measures resistance or porosity of cell sheets in culture. These measurements can only be applied to highly confluent and organized layers of epithelial and sometimes endothelial cells. Recently Molecular Devices Corporation (Palo Alto, Calif.) has introduced a cell microphysiometer that electrically follows the pH in the microenvironment about a few thousand cells. To be effective this device must be used in special medium that lacks buffers—a serious drawback for many applications.

Most animal cells in culture will only multiply when they are attached to a surface and are provided with the necessary nutrient medium and environment. Usually this surface or substratum is glass or specially treated polystyrene. Proteins from the medium will spontaneously absorb to these substrata and hence the surface encountered by the cells is always protein coated. The tissue culture is started or seeded when a cell suspension is added to a petri dish or other vessel, placed in a warm (37° C.) environment and left undisturbed.

As suspended cells settle onto the protein-coated surface, they form attachments to the absorbed proteins over a period of about 30 minutes. Following this, a striking series of changes takes place in the cell's morphology. Attached to a substratum, the cells begin a process referred to as spreading as they flatten and extend themselves out on the surface. In time, they go from spheres of approximately 20 micrometer diameter to flattened forms with dimensions as large as 100 micrometers in the plane of the substratum and a thickness of only a few micrometers. This dramatic change in the cell's shape takes place over a period of a few hours dependent upon the type of cell and the protein that coats the substratum. Once anchored, cells display another remarkable behavior. By extending portions of the cell cytoplasm forward and away from the main cell body, making an attachment and then pulling the back of the cell up, the cell crawls about on the surface with a speed of a few micrometers per hour. Motility in tissue culture is found for almost all animal cells. These motions are generated in an outer band of cytoplasm and involve the cytoskeleton of the cell, in particular muscle-like strands of the protein actin referred to as microfilaments. This phenomenon which is observed in vitro is thought to be an expression of a basic cellular mechanism involved in processes including wound healing, maintenance of cellular organization in tissues, surveillance for invading foreign organisms, and development of the early embryo.

If conditions are suitable, the cell will copy its chromosomes in preparation for cell division. In mitosis, the highly spread cell retracts from the surface and again becomes spherical in morphology. When mitosis is complete, the cell splits into two spherical daughter cells. These new cells now initiate the spreading process and in a few minutes spread out again upon the substratum into a highly flattened morphology and the cycle begins anew. Tissue culture is an indispensable research tool. In addition, it has played an essential role in the development of modern biotechnology. Some of the powerful new applications are: pharmaceuticals, monoclonal antibodies, vaccines, genetic screening, skin grafts, gene therapy and in vitro toxicology.

SUMMARY OF THE INVENTION

The present invention measures cellular activities which were previously difficult to follow in any but a qualitative manner. The invention also measures fluctuations in the height of spaces beneath cells which has not been done previously. The apparatus of the invention provides measurements that, for the most part, can be followed continuously and in real time. The apparatus is sensitive enough to detect activities of even single cells, although generally a population of about 20-50 cells is followed.

The invention has been used to monitor the activities of living eukaryotic animal cells grown in tissue culture and has potential applications as a whole cell biosensor. According to the invention electrodes are deposited by vacuum evaporation in two layers at the bottom of a tissue culture enclosure. AC current of about one microamp and fixed or varying frequencies is applied between a large counter electrode and a small active electrode, while the voltage is monitored with a phase sensitive detector. Since this is a two probe measurement, the active electrode is made small, such that its impedance dominates the measurement. In the apparatus of the invention, cells are cultured directly on the small electrodes. As they attach and spread (flatten out) on the electrode surface they cause large changes in electrical impedance of the system. These changes are highly dependent on the type of protein initially absorbed on the electrode surface. Following attachment and spreading cell motion causes cell contacts with the electrode to change with time, and this in turn causes fluctuations in the electrode's impedance. In confluent monolayer cultures of fibroblasts for example, approximately 20 cells cover a $10^{-4}$ cm$^2$ electrode, but the invention is readily capable of detecting the activities of single cells.

In addition to detection of cell attachment, spreading and lateral motion, the invention also shows that by varying the applied AC signal frequency, several other parameters related to cell morphology and activity can be measured. At appropriate frequencies the porosity of the cell layer itself can be measured. It is know that cells in culture do not directly contact surfaces except for small foot-like adhesion plaques. At low AC frequencies, it is possible to estimate the extent of the cell that is involved in these very close contacts.

The cell-covered electrode impedance measured with this invention has been modelled assuming that current flows uniformly and radially through the solution-filled space beneath the cell. Using impedance measurements over a range of AC frequencies, the average thickness of this space can be calculated. In addition, changes in this average spacing in confluent layers of cells where lateral motion is inhibited can be measured with great precision. Average changes as small as one Angstrom can be measured. This extreme sensitivity is one of the unique features of the invention.

By using the apparatus and method of the invention, the activities of cultured cells that are attached to surfaces can be followed continuously and in real time. The invention can detect and measure the following: cell attachment, cell spreading, lateral motion of cells, impedance of cell sheets (porosity), areas involved in adhesion plaques, cell-substrate spacing, and vertical cell motion.

The ability of the inventive electric field apparatus to detect the response of cells to changes in the physical environment and to drugs and other biologically active compounds has been demonstrated with several lines of human and murine fibroblasts and with murine macrophage and bovine endothelial cells.

The electronics of the invention are connected to arrays of electrodes. These electrode arrays have applications in situations where the response of cells in culture to any chemical, biological, or physical agents is being sought. Electrode pairs are placed in isolated culture vessels and cells are independently exposed to different regimens. Using switches or a switching device, each culture is followed for impedance changes using a single lock-in amplifier/computer. In this manner, information regarding the cultured cells such as their dose-response to a specific agent are determined in a single run.

In addition to having electrodes mounted within a separate culture chamber, multiple electrodes may be used within the same culture chamber. In this situation, one could readily obtain duplicate measurements of the same culture. Such data provides an indication of heterogeneity within the culture or may be used to obtain an average cell response.

The invention has several applications as a whole cell biosensor which include, but are not limited to:
(1) The monitoring of conditions within reactors used in mass culturing mammalian and other eukaryotic cells;
(2) The testing of compounds for cytotoxicity;
(3) The testing of the efficacy of drugs;
(4) The monitoring of environments of toxic compounds; and
(5) Research in cell biology and tissue culture to detect cell motility, metabolic activity, cell attachment and spreading, cell layer porosity and cell morphology.

The invention is useful for toxicity measuring because more complex in vitro behaviors appear to be valuable predictors of animal response to compounds; cell-substratum interactions including spreading and cell motility fit in this category. These activities require a complex series of events to take place in a regulated, integrated fashion. Locomotion, for example involves regulation of metabolic energy supplies; formation, contraction and breakdown of actin microfilaments; formation and breakdown of interactions with the substratum, etc. When cells are exposed to a toxic compound, the chemical may act at any point in this cascade of events and alter the motility measurement. In this aspect, measurements of complex in vitro behaviors more closely parallel studies using whole animals where toxic responses can result from a variety of mechanisms.

The difficulty in using cell-substratum interactions in toxicology is that they have been very difficult to quantify. Generally cell attachment and spreading is observed microscopically and the morphology of the cells described in qualitative terms. Some procedures have been devised to quantify cell attachment and spreading, but most of these methods ultimately require the sacrifice of the culture for staining and are rather susceptible to human errors. The problems of detecting cell motion are more difficult. Even so-called rapid motions of cells in culture require time lapse cameras for detection. This form of data is exceptionally difficult to quantify and usually requires image processing coupled with extensive data manipulation. In addition, to follow cell motion, one is limited to sparse cultures where individual cells can be readily identified. The present invention addresses and solves each of these problems.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which the preferred embodiments of the invention are illustrated.

DESCRIPTION OF THE PREFERRED EMBODIMENT

Figure 1:
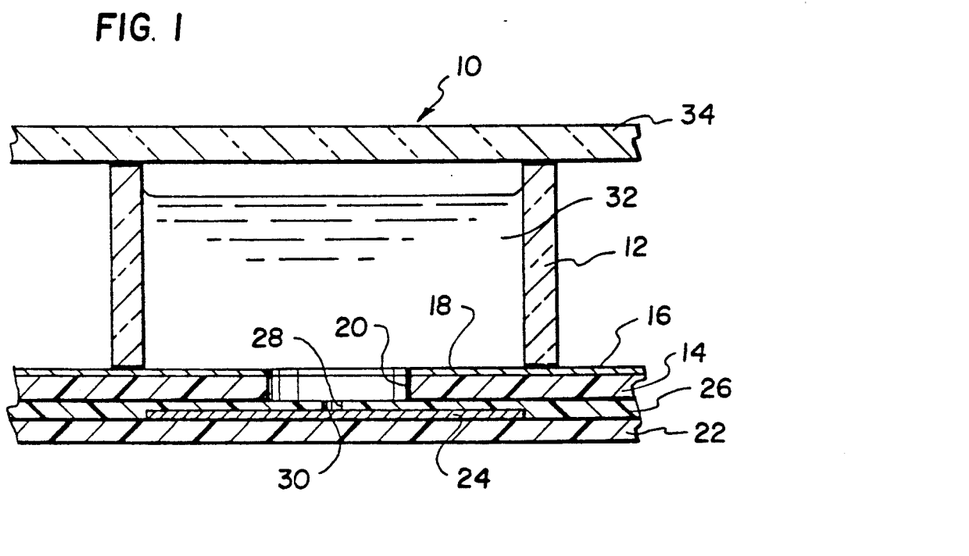
FIG. 1 is a sectional view of a single cell culture well assembly used in the multiple electrode array of the present invention.
Figure 2:
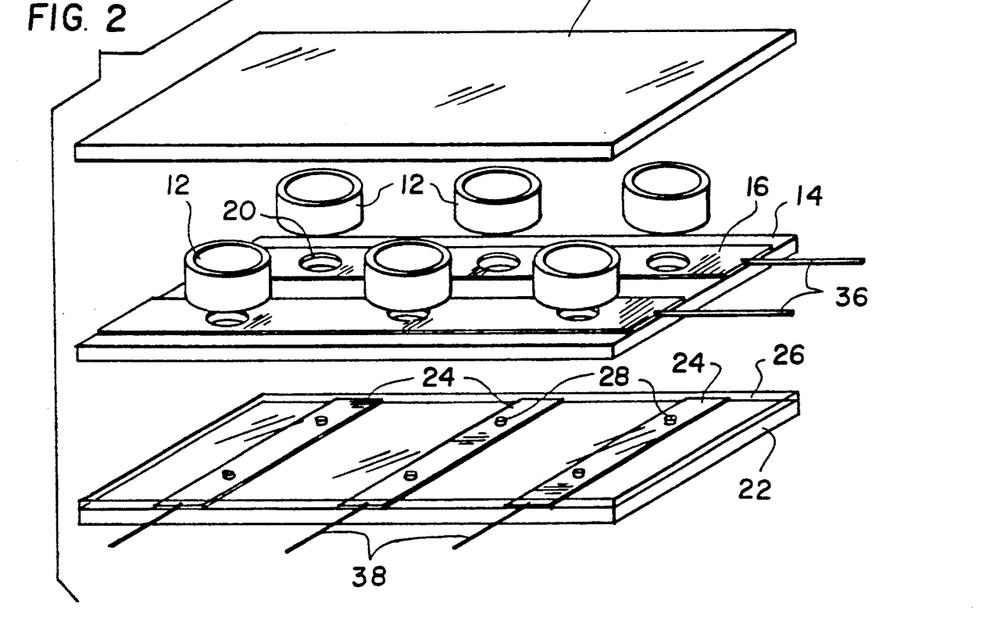
FIG. 2 is an exploded view of the multiple electrode array of the present invention.

Referring to the drawings in particular, the invention embodied in FIG. 1 and 2 comprises a multiple electrode array apparatus which includes a plurality of cell culture well assemblies generally designated 10 in FIG. 1. As shown in the exploded view of FIG. 2, six well assemblies form a single array in the illustrated embodiment of the invention. The principles of the invention can be applied to any number of well assemblies however, and is particularly suited to a number of assemblies which can be distributed in a rectilinear pattern, e.g. 6, 12, 24 and 96 well assemblies. The selection of the well configuration and number is made to match multiple well plates which are commonly used in tissue culture procedures.

Each well assembly 10 comprises a well wall or cylinder 12 made of glass, treated polystyrene, or other bio compatible, rigid material. Cylinder 12 is sealed to the upper surface of an upper substrate 14, which, as best shown in FIG. 2, carries a first plurality of electrode strips 16 made of gold or other bio-compatible conductive material. Strips 16 are advantageously vapor deposited as a thin film on the substrate 14 which is made of electrically insulating material. The area within the circumference of cylinder 12 defines a large upper electrode 18 containing a cylindrical hole 20 which also extends through the upper substrate 14 to expose the upper surface of an insulating layer 26. Insulating layer 26 is advantageously in the form of a photoresist. Insulating layer 26 coats the upper surface of a lower substrate 22 and the upper surface of a second plurality of electrode strips 24 which are also advantageously made of gold and extend transversely to the strips 16. Photoresist layer 26 includes a small hole 28 positioned within the hole 20 for each well assembly 10, to expose a small electrode area 30 of the strip 24. Strips 24 may be vapor deposited in thin films on an insulating material forming substrate 22 in the same method used to deposit the strips 16 on substrate 14. Area 30 which is exposed in hole 28 forms a small electrode which operates in conjunction with the large electrode 18. Advantageously, the small electrode 30 in each assembly should have an area which is less than or equal to about $10^{-2}$ cm$^2$, or advantageously $10^{-3}$ to $10^{-4}$ cm$^2$.

The substrates 14 and 22 are connected to each other by water resistant adhesive and a lid plate 34, advantageously made of the same material as cylinders 12, is placed over all of the wells to close the interior space of each well which is at least partly filled with an electrolytic tissue culture medium 32 having appropriate nutrients for maintaining cells to be monitored by the present invention. The medium is understood to extend into the holes 20 and 28 and be in contact with the large and small electrode areas 18, 30.

Figure 3:
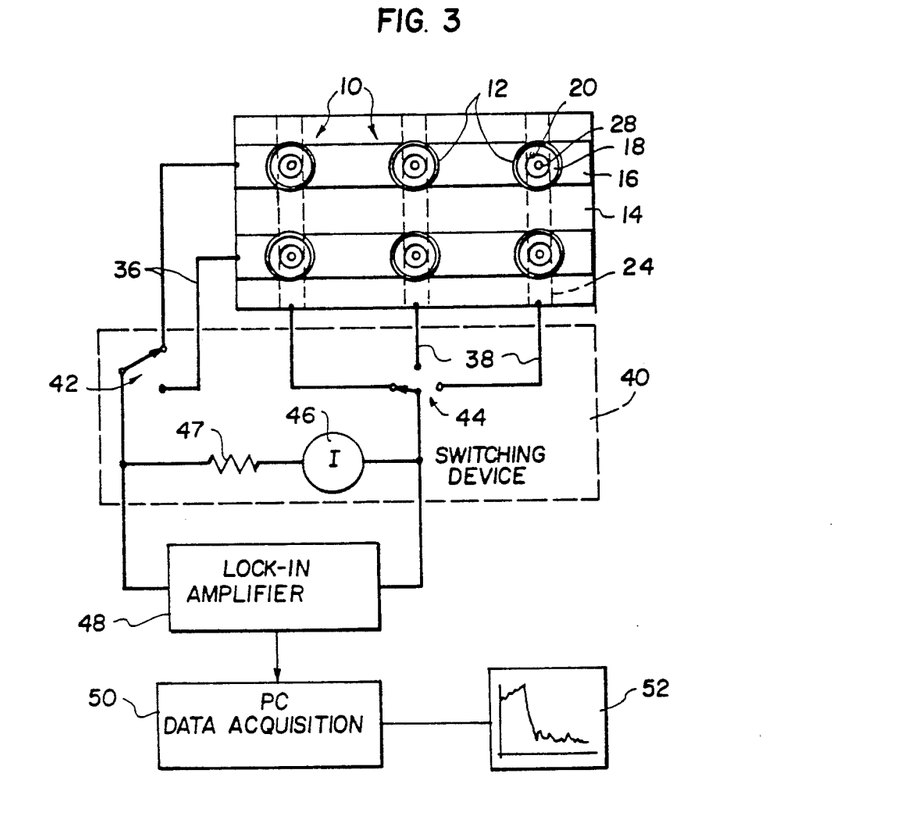
FIG. 3 is a schematic diagram illustrating the multiple electrode array connected to additional apparatus for practicing the present invention.

Each well assembly 10 is individually monitored by leads 36 connected to strips 16 which are used in conjunction with leads 38 connected to strips 24. As shown in FIG. 3, a switching device 40 containing schematically illustrated switches 42 and 44 are connected to the leads 36 and 38. The switches are automatically and selectively operated by known multiplexing means so that a signal can be applied to each individual well assembly by selection of the appropriate electrode strips from the first and second plurality of strips.

The selected area for the small electrode 30 is an essential feature of the present invention. With larger electrode areas, cell-related signals become difficult to detect. This is because the resistance of the medium is larger than the electrode's impedance and this masks changes due to the cells. When electrodes are reduced to the selected area, the activities of the cells are clearly revealed because now, the electrode impedance is dominant. The size of the electrode restricts the maximum cell population that can be observed to about 50 cells but it should be noted that the activities of even a single cell can be measured easily using the present invention.

Switching device 40 includes a power supply 46 which is capable of applying an AC signal at low current (e.g. 1 microamp) and fixed or variable frequency (e.g. 4 kHz) between each electrode pair for each well assembly. The current applied between the small electrode and large counter electrode produces a voltage which is monitored by a lock-in amplifier 48 connected across the power supply 46 and a load resistor 47. Voltage and phase data are supplied to and, stored and processed within a personal computer 50 which displays the results on a display 52 which may be a video display, a chart recorder or other known display mechanism. Computer 50 also controls the output of the amplifier and the position of the switches 42, 44 to service the different electrode pairs and various times during the course of an experiment.

Figure 4:
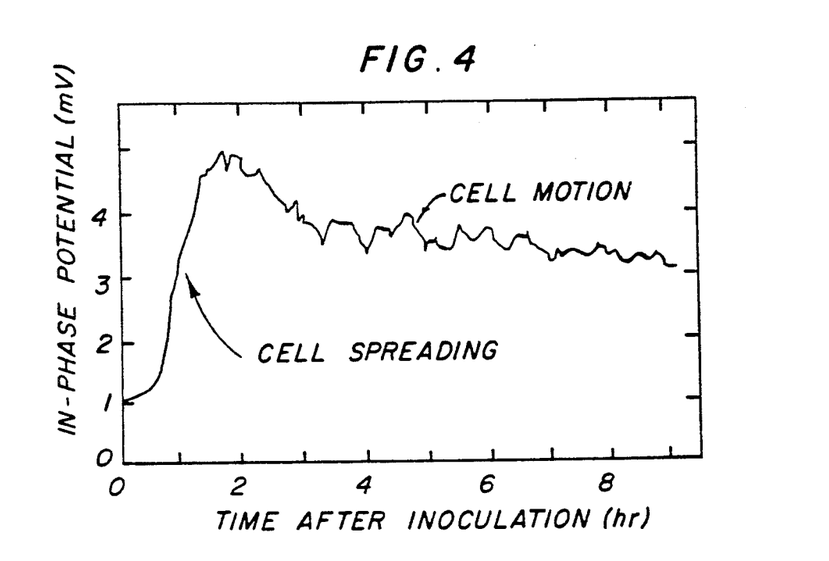
FIG. 4 is a graph plotting typical measured potential against time after the establishment of a cell culture in the apparatus of the present invention.

FIG. 4 illustrates the results for the application of a constant AC signal of 1 microamp at 1 volt and 4 kHz frequency with a 1 mega ohm resistor as load resistor 47. FIG. 4 illustrates the case where murine skin cells (3T3 fibroblasts) approximately $10^5$ cells/cm$^2$ were inoculated on the electrodes at time=0. As the cells attached and spread on the electrode surface, they acted as insulating particles due to their membranes. The cells spread during approximately the first one and one half hours after inoculation.

By effectively blocking the area available for current flow, a large increase occurred in the impedance of the system. This generally peaked a few hours into the experiment. Smaller changes in the cell-electrode interaction due to cell motions caused the impedance to fluctuate with time. It is in this general manner that the apparatus of the present invention can return information regarding cell-surface interaction and cell motility.

It is important to understand that the apparatus and method of the present invention detects the activity of cells electrically since the cells effect the impedance measurement. The cells themselves are not effected by the low AC current or the weak electrical fields however. The non-invasive nature of the measurement has been established in many experiments. No effects of the electrical measurement on the cultured cells have been detected. Typically, the magnitude of the voltage drop across the open electrode is on the order of a millivolt and increases to several millivolts with a confluent cell layer. The data is sometimes presented as a voltage in- or out-of-phase with the applied signal, but more accurately, the data is converted to an equivalent in-series resistance and a capacitance.

To verify that the fluctuations in impedance are due to living cells, rather than noise in the system, experiments were conducted with normal human lung fibroblast. This showed characteristic fluctuations similar to those in FIG. 4. The cells were then killed with a 1% formalin solution. Subsequent measurements displayed a flat line showing no activity what-so-ever. This proved the biological nature of the fluctuations and that any electronic noise in the system is considerably below the level of measurements for biologically caused fluctuations.

The present invention also includes the discovery that various characteristics of the cells can be monitored by changing the frequency of the current applied between the large and small electrodes.

It is known that fibroblastic cells in culture attached to the substrate by a few small foot-like projections leaving spaces or channels between the ventral surface of the cell and the substrate. Although much work leading to the present invention was conducted at a frequency of 4 kHz, if differed frequencies are utilized, the amount of current flowing in these channels, and thus the impedance, would vary.

Figure 5:
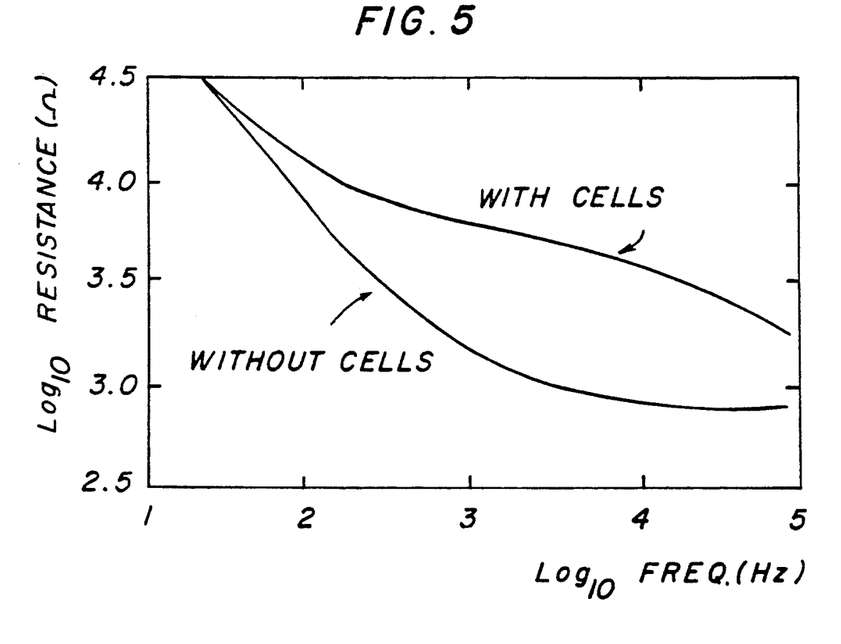
FIG. 5 is a graph plotting resistance (treating the cell-electrode system as a series RC circuit) against frequency on a log-log scale for the apparatus of the invention.
Figure 6:
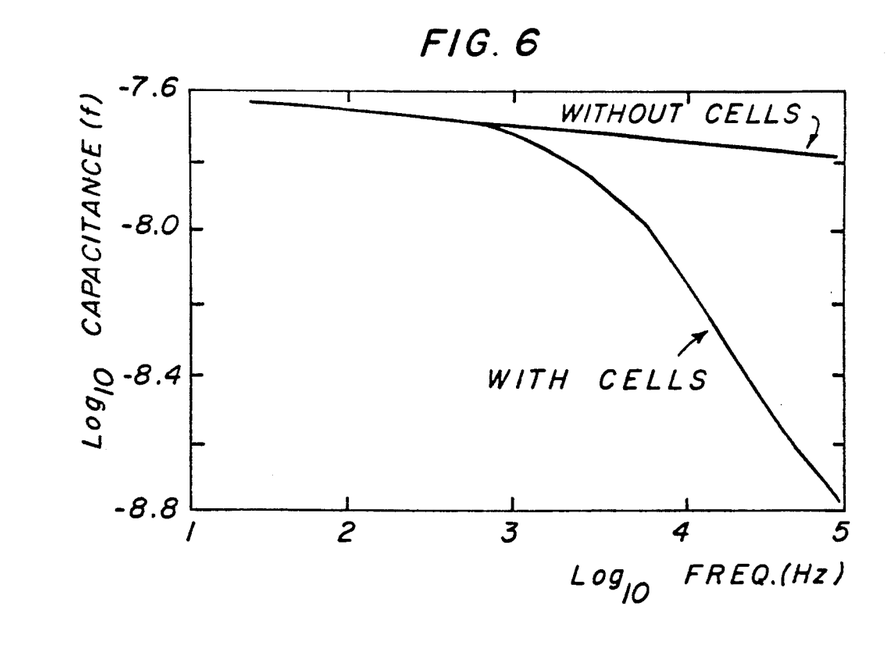
FIG. 6 is a graph similar to FIG. 5 plotting the capacitance against the frequency.

This is clearly illustrated in FIGS. 5 and 6 which respectively show the resistance and capacitance as it changes with frequency, for the case where no cells are present and for the case where cells are present. FIGS. 5 and 6 show typical results for a small electrode (area $1.06 \times 10^{-3}$ cm$^2$), with and without a confluent layer of WI38 VA13 fibroblasts as a function of applied AC frequency. Note that the circuit is regarded as a resistor and capacitor in series and that this is a log-log plot. A more sensitive result can be obtained by plotting normalized resistance and capacitance. These unit-less values are obtained by dividing the values for a cell-covered electrode at different frequencies with the corresponding values for a naked electrode.

Figure 7:
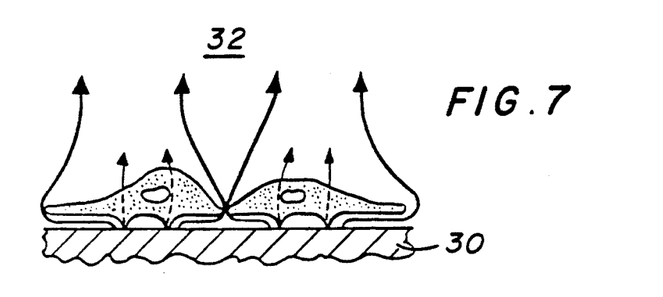
FIG. 7 is a schematic representation of a model for cell positioning on the small electrode, which closely fits experimental results achieved with the invention.
Figure 8:
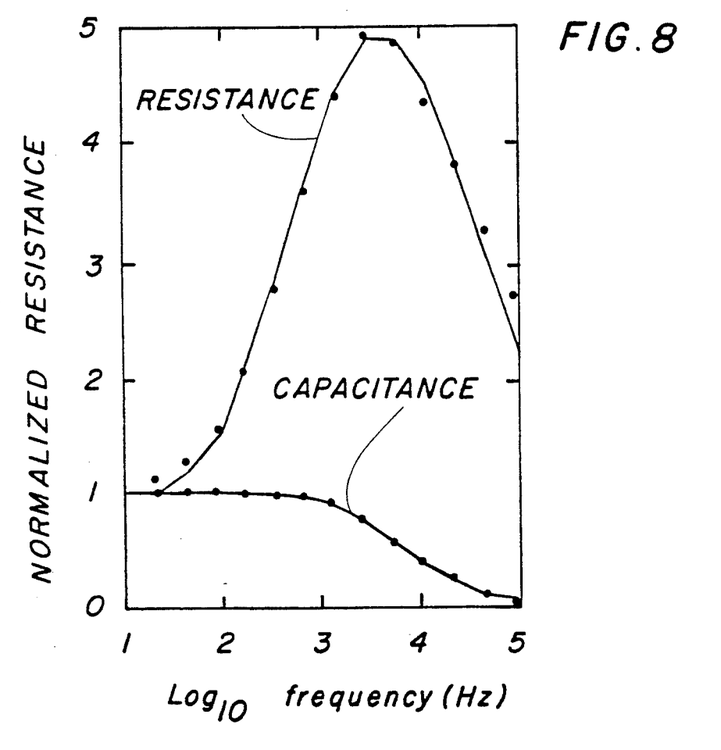
FIG. 8 is a graph plotting the ratio of resistance and of capacitance for a cell-covered electrode to that of a naked electrode against frequency which compares calculated values following the model of FIG. 7 to experimental values with the inventive apparatus.

This was first done with the assumption that the ventral or bottom surface of the cell was in full contact with the small electrode. The calculated results did not match the experimental results. The assumption was then made that the cells contacted the electrode only at the foot-like projections. Under these conditions, the calculated results closely matched the experimental results. A further even more accurate model which is illustrated in FIG. 7, assumes electrode contact only at the foot-like projections, and also assumes an expected resistance between cells. FIG. 8 shows the calculated results as dots and the experimental results as lines. The close fit between the model and the actual result is clearly evident. The model of FIG. 7 provides two adjustable parameters, one being the height of the cell above the electrode and the other, the resistance between the cells in the confluent layer. For the WI-38 VA13 cells, the first adjustable parameter was calculated to be 13.3 nanometers for the height of the cells above the electrode, and 1.1 ohm cm$^2$ for the resistance of the confluent layer.

Using the model of FIG. 7, fluctuations in impedance can be related to small changes in, for example, the average height of the channels between the cells. Calculations have shown that variations in the cell height of only a few nanometers can be readily detected in the impedance fluctuations. This is far below optical resolution and indeed no motion of the cells can be seen if they are simultaneously observed in a microscope. The invention thus provides extreme sensitivity for detecting changes in the cell-substrate spacing and in cell motility. These two factors are effected in various ways by different chemicals and environmental conditions. For this reason, the invention can be used for quantitative toxicology and testing.

Figure 9:
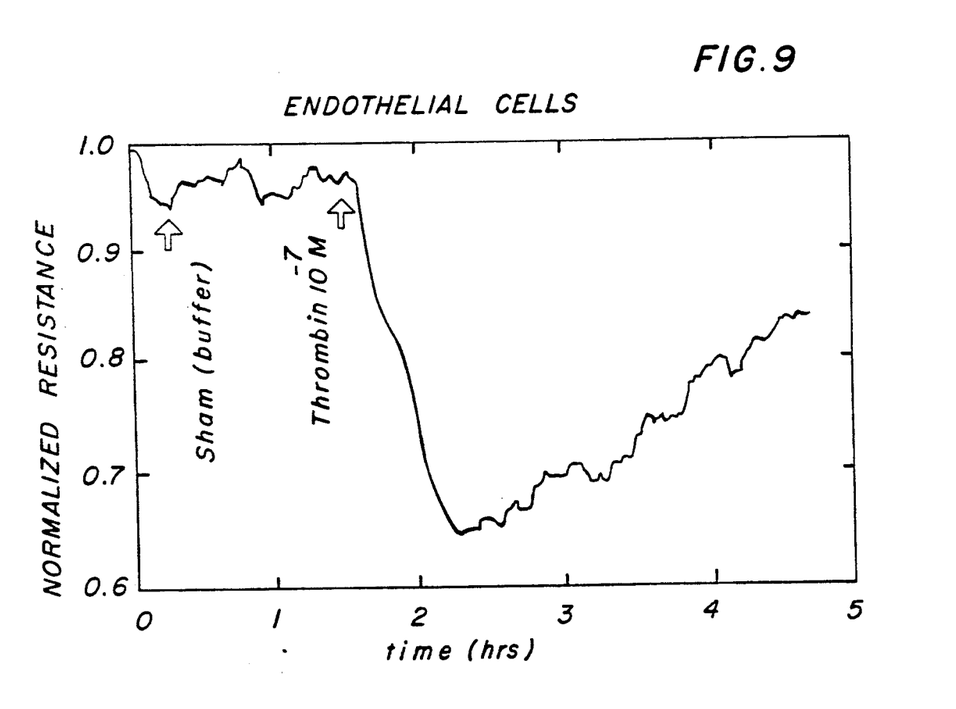
FIG. 9 is a graph plotting a normalized resistance value against time to illustrate a chemical response which can be quantified by the invention.

FIG. 9 shows the results conducted on bovine pulmonary endothelial cells which were grown on the inventive apparatus. The cells gave considerably different impedance changes as a function of time than the fibroblasts or macrophages which were also tested using the invention. Heavy inoculations resulted in slow increase in impedance that last over several days instead of a few hours with most cells. During this time, the cell monolayer was observed to organize into a more ordered cobblestone-like pattern. When endothelial cells in this state were exposed to $10^{-7}$M thrombin, there was a large drop in measured impedance as shown in FIG. 9. This fits other data well that suggest thrombin increases the permeability of the cell layers and thus reduces the electrical impedance. Large impedance changes were also observed for low levels of histamine. FIG. 9 also shows the lack of any significant effect when a sham buffer solution was used as a control.

Figure 10:
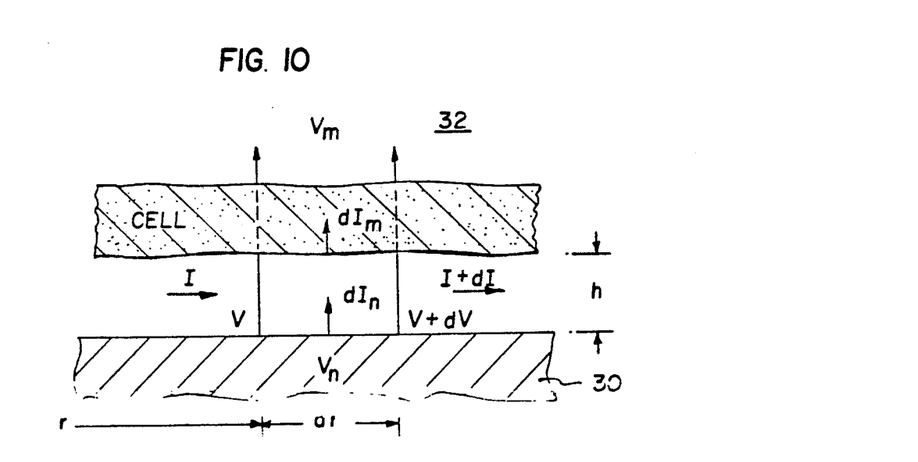
FIG. 10 is a schematic model showing the interaction between a cell and an electrode of the invention.

A quantitative analysis for the monitoring capacity of the present invention has also been derived. FIG. 10 is a schematic representation which emphasizes the space between the cell and the electrode. The calculated resistance is due to the current flow under the cell, and an additional resistance because the current must flow out between the cells. The broken line represents capacitive current flowing through the cell membranes. The cells are regarded as disk-shaped when viewed from the top. The schematic side view diagram of FIG. 10 is useful in constructing the differential equations of the present invention, in these equations $v$ is the frequency of the applied AC current I, $\rho$ is the resistivity of the solution, $Z_n(v)$ is the specific impedance of the cell-free electrode-electrolyte interface, and $Z_m(v)$ is the specific membrane impedance of the cells. If the capacitance, of the cell membrane is 1 $\mu$F cm$^2$, then $Z_m = -i/2\pi v(C/2)$.

Referring to the parameters and dimensions of FIG. 10 where h is the height of the cell above the electrode, r is the radius of the cells which are approximately a circular disk:

$$-dV = \frac{\rho dr}{h 2\pi r} I \quad (1)$$

$$V_n - V = \frac{Z_n(v)}{2\pi r dr} dI_n \quad (2)$$

$$V - V_m = \frac{Z_m(v)}{2\pi r dr} dI_m \quad (3)$$

$$dI = dI_n - dI_m \quad (4)$$

$$\frac{d^2V}{dr^2} + \frac{1}{r} \frac{dV}{dr} - \gamma^2 V + \beta = 0 \quad (5)$$

where $$\gamma^2 = \frac{\rho}{h} \left[ \frac{1}{Z_n} + \frac{1}{Z_m} \right] \quad (6)$$

and $$\beta = \frac{\rho}{h} \left[ \frac{V_n}{Z_n} + \frac{V_m}{Z_m} \right] \quad (7)$$

where $V_n$ is the potential of the electrode and $V_m$ is the potential measured in the solution just outside the cell layer. The solution of equation (5) is a sum of the modified Bessel functions of the first kind of order 0 and 1. By using proper boundary conditions, the specific impedance for a cell-covered electrode can be written $$\frac{1}{Z_c} = \frac{1}{Z_n}\left[\frac{Z_n}{Z_n + Z_m} + \frac{\frac{Z_m}{Z_n + Z_m}}{\frac{i\gamma r_c}{2}\frac{I_0(\gamma r_c)}{I_1(\gamma r_c)} + 2R_\beta\left(\frac{1}{Z_n} + \frac{1}{Z_m}\right)}\right] \quad (8)$$

Note that the solution depends upon only 2 parameters, $R_b$, the resistance between the cell for a unit area and $\alpha$ defined by:

$$\gamma r_c = r_c\sqrt{\frac{\rho}{n}\left(\frac{1}{Z_n} + \frac{1}{Z_m}\right)} = \alpha\sqrt{\frac{1}{Z_n} + \frac{1}{Z_m}} \quad (9)$$

Since $Z_n$ is measured and $Z_m$ is basically the impedance of a two-cell membrane in series, $\alpha$ is the only adjustable parameter in equation (9). The frequency dependence does not appear explicitly in the equation as it is contained within the impedances $Z_n$ and $Z_m$.

The best fit for the WI38 VA13 cell data is obtained with $\alpha = 7$ ohm$^{\frac{1}{2}}$ cm, $R_b = 1.1$ ohm cm$^2$. Both the average radius of the cells, 11 micrometers, and the resistance of the tissue culture medium, 54 ohm-cm, were obtained for independent measurements. This gives an average calculated channel height of 13.3 nanometers.

While a specific embodiment of the invention has been shown and described in detail to illustrate the application of the principles of the invention, it will be understood that the invention may be embodied otherwise without departing from such principles.

What is claimed is:

1. An apparatus for monitoring cell-substrate impedance, comprising:
    means defining a plurality of separate tissue culture chambers in a matrix, each tissue culture chamber having a solid growth surface on which a tissue culture containing a multiplicity of cells may grow, the cells having ventral surfaces at least partly in contact with the growth surface;
    a measuring electrode directly on each growth surface, each measuring electrode having an area of less than $10^{-2}$ cm$^2$ so that the ventral surfaces of from 1 to about 50 cells are at least partly in contact with the measuring electrode;
    means for measuring impedance of the cells in at least partial contact with the measuring electrode, connected to the measuring electrode of each tissue culture chamber, said means for measuring impedance including a reference electrode in each tissue culture chamber which has an area that is greater than the area of the measuring electrode, an upper substrate (14) having a first electrode layer (16) thereon, the upper substrate having a plurality of first holes (20) therethrough which extend through the first electrode layer, each first hole being in one of the tissue culture chambers;
    a plurality of well walls (12) engaged on the upper substrate around respective first holes and around at least a portion of the first electrode layer to define the reference electrodes (18) around at least a portion of each first hole, the plurality of well walls comprising the means defining the plurality of separate tissue culture chambers;
    a lower substrate (22) engaged under the upper substrate, the lower substrate having a second electrode layer (24) thereon extending between the upper and lower substrates and under at least a portion of each first hole;
    an insulation layer (26) between the upper substrate and the second electrode layer extending at least under each first hole, the insulation layer having a plurality of second holes (28) therethrough and in each respective first hole for exposing areas of the second electrode layer to define the measuring electrodes (30) in the first hole;
    the means for measuring impedance including electric power means (46) connected between the measuring and reference electrodes for applying electric power between the electrodes, and electric impedance monitoring means (48) connected between said measuring and reference electrodes for monitoring electric impedance between the electrodes.

2. An apparatus according to claim 1 wherein said means for measuring impedance includes means for applying an alternating current to the small measuring electrode in each chamber.

3. An apparatus according to claim 2 wherein said means for applying an alternating current includes means for varying the frequency of the alternating current.

4. An apparatus according to claim 1 wherein the area of each small measuring electrode is from about $10^{-3}$ cm$^2$ to $10^{-4}$ cm$^2$.

5. An apparatus according to claim 1, wherein the plurality of separate tissue culture chambers are aligned in rows and columns, the measuring electrode of each tissue culture chamber in each row being connected in series to each other, each reference electrode in the chambers of each column being connected in series to each other, said means for measuring impedance addressing the measuring and reference electrodes in each tissue culture chamber by connection to the series connected electrode of each column and row of each tissue culture chamber respectively.

6. An apparatus according to claim 1, wherein said electric power means includes switching means for selectively applying electric power to the electrodes of each tissue culture chamber, the electric impedance monitoring means being connected to the switching means for monitoring electric impedance between the electrodes of each tissue culture chamber.

7. An apparatus according to claim 6, wherein said first electrode layer forming the reference electrode of each tissue culture chamber comprises a plurality of first conductive strips extending in a first direction on said upper substrate, said second electrode layer forming the measuring electrode of each tissue culture chamber comprising a plurality of second conductive strips extending on said lower substrate in a second direction which is at a non-zero angle to said first direction, said switching means being selectively connected to one of said first conductive strips and one of said second conductive strips for applying power to and monitoring impedance from the electrodes of each tissue culture chamber.

8. An apparatus according to claim 7, wherein said first direction is perpendicular to said second direction.

9. An apparatus according to claim 8, wherein said conductive strips are made of gold.

10. An apparatus according to claim 8, wherein the second hole of each tissue culture chamber is up to $10^{-3}$ cm$^2$ in area.

11. An apparatus according to claim 10, wherein said power supply means includes means for applying an AC current between the electrodes of each tissue culture chamber.

12. An apparatus according to claim 11, including means for varying a frequency of the AC current applied to the electrodes by about 10 to 100,000 HZ for varying the impedance measured by said electric impedance monitoring means in a quantitative manner and to obtain information regarding cell morphology.

* * * * *